United States Patent
Devin-Baudoin et al.

(10) Patent No.: US 6,824,764 B2
(45) Date of Patent: Nov. 30, 2004

(54) USE OF PARTICULAR AMINOSILICONES AS A PRETREATMENT OF PROCESSES FOR COLORING KERATIN FIBERS WITH DIRECT DYES OR WITH OXIDATION DYES

(75) Inventors: Priscille Devin-Baudoin, Vanves (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 117 days.

(21) Appl. No.: 10/290,209

(22) Filed: Nov. 8, 2002

(65) Prior Publication Data

US 2003/0121109 A1 Jul. 3, 2003

(30) Foreign Application Priority Data

Nov. 8, 2001 (FR) ............................................ 01 14483

(51) Int. Cl.$^7$ ................................................ A16K 7/00
(52) U.S. Cl. .................... 424/70.1; 424/70.2; 424/70.6; 424/70.11; 424/70.12; 424/70.122; 8/405; 8/406; 8/410; 8/421; 8/581; 8/632
(58) Field of Search .............................. 424/70.1, 70.2, 424/70.6, 70.11, 70.12, 70.19, 70.122; 8/405, 406, 410, 421, 581, 632

(56) References Cited

U.S. PATENT DOCUMENTS 4,710,314 A * 12/1987 Madrange et al. .......... 510/122

FOREIGN PATENT DOCUMENTS

| DE | 197 54 053 | 6/1999 |
|---|---|---|
| EP | 0 890 355 | 1/1999 |
| GB | 2 165 550 | 4/1986 |

OTHER PUBLICATIONS

English language Derwent Abstract of DE 197 54 053, Jun. 10, 1999.

* cited by examiner

Primary Examiner—Brian P. Meuk
Assistant Examiner—Eisa Elhilo
(74) Attorney, Agent, or Firm—Finnegan, Henderson, Farabow, Garrett & Dunner L.L.P.

(57) ABSTRACT

The present disclosure relates to the use, as a pretreatment of a process for coloring, with at least one direct dye and/or with at least one oxidation dye, keratin fibers, such as human hair, of a composition comprising at least one particular aminosilicone as defined herein.

The disclosure also relates to a process for coloring, with at least one direct dye and/or with at least one oxidation dye, keratin fibers, such as human hair, comprising a pretreatment with a composition comprising at least one particular aminosilicone as defined herein.

58 Claims, No Drawings

USE OF PARTICULAR AMINOSILICONES AS A PRETREATMENT OF PROCESSES FOR COLORING KERATIN FIBERS WITH DIRECT DYES OR WITH OXIDATION DYES

The present disclosure relates to the use, as a pretreatment, in a process for colouring keratin fibres, such as hair, with at least one direct dye and/or with at least one oxidation dye, of a composition comprising at least one particular aminosilicone, as defined herein.

The disclosure further relates to a process for colouring, with at least one direct dye and/or with at least one oxidation dye, keratin fibres, such as human hair, comprising a pretreatment with a composition comprising at least one particular aminosilicone, as defined herein.

Two main types of processes for colouring keratin fibres exist: direct dyeing and oxidation dyeing. Direct dyeing uses, in the presence or absence of at least one oxidizing agent, at least one direct dye and/or at least one pigment, which comprise coloured molecules. Direct dyeing may give the fibres a temporary colour that fades out after a few shampooings. Oxidation dyeing uses at least one oxidation dye precursor and at least one oxidizing agent. Oxidation dyeing may give the fibres a more resistant colour than direct dyeing.

There is at least one need to improve the rise of coloration on fibres, such as sensitized fibres, which may be more porous and may fix the at least one colouring agent to a lesser degree.

The use of at least one oxidizing agent may result, for example, in degradation of the keratin fibre.

There exists at least the need to limit this degradation and its consequences on the cosmetic condition of the fibre.

After considerable research, the inventors have discovered, surprisingly and unexpectedly, that the use, as a pretreatment on keratin fibres, such as human hair, of a composition comprising at least one particular aminosilicone as defined herein, allows at least one of the above problems to be solved.

This pretreatment may also improve, for example, the resistance of coloration obtained with at least one direct dye and/or with at least one oxidation dye, for example, with respect to shampooing.

Another new embodiment relates to the use, as a pretreatment of a process for colouring, with at least one oxidation dye and/or with at least one direct dye, keratin fibres, such as human hair, of a composition comprising at least one aminosilicone chosen from formulae (I) and (II).

Another new embodiment improves the rise of the colour, for example, on sensitized hair, and/or the condition of the fibre after coloration, such as in the case of coloration with at least one oxidizing agent. The resistance to shampooing of the colorations may also improve.

The phrase "improvement in the condition of the fibre" means, for example, a reduction in the porosity and/or the alkaline solubility of the fibre and a potential improvement in the cosmetic properties, such as smoothness, softness and ease of disentangling and of styling.

This effect may be remanent, e.g., long-lasting.

The porosity may be measured by fixing at 37° C. and at pH 10, for two minutes, 2-nitro-para-phenylenediamine at 0.25% in an ethanol/pH 10 buffer mixture (10/90 volume ratio).

The alkaline solubility may correspond to the loss of mass of a sample of 100 mg of keratin fibres under the action of decinormal sodium hydroxide for 30 minutes at 65° C.

Another new embodiment relates to a colouring process comprising: applying to keratin fibres, such as human hair, a composition comprising at least one aminosilicone chosen from formulae (I) and (II); optionally rinsing the fibres; applying at least one direct dye and/or at least one oxidation dye composition for a period sufficient to develop the colour; optionally rinsing the fibres; optionally shampooing the fibres; and optionally drying the fibres.

Aminosilicone(s)

The at least one aminosilicone is chosen from formulae (I) and (II):

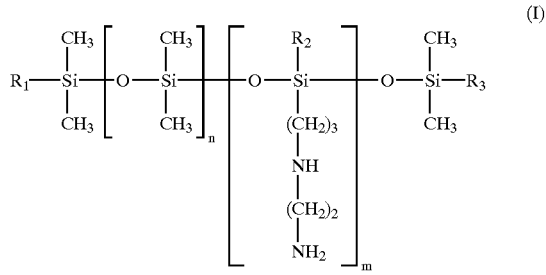

(I)

wherein:
  m and n are chosen from numbers such that the sum (n+m) ranges from 1 to 1000 and, for example, from 50 to 250, and further, for example, from 100 to 200;
  n ranges from 0 to 999, for example from 49 to 249, and further, for example, from 125 to 175, and m ranges from 1 to 1000, for example, from 1 to 10, and further, for example, from 1 to 5;
  $R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals.

The alkoxy radical may be, for example, a methoxy radical.

The hydroxyl/alkoxy molar ratio may range, for example, from 0.2:1 to 0.4:1, for example, from 0.25:1 to 0.35:1, and further, for example, may be 0.3:1.

The at least one aminosilicone of formula (I) may have a weight-average molecular mass ranging from 2000 to 1000000, for example, from 3500 to 200 000.

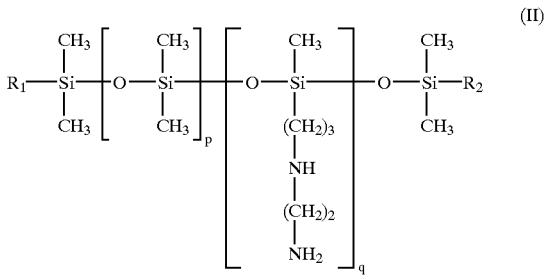

(II)

wherein:
  p and q are chosen from numbers such that the sum (p+q) ranges from 1 to 1000, for example, from 50 to 350, and further, for example, from 150 to 250;
  p ranges from 0 to 999, for example, from 49 to 349, and further, for example, from 159 to 239, and q ranges from 1 to 1000, for example, from 1 to 10, and further, for example, from 1 to 5; and
  $R_1$ and $R_2$, which are different, are chosen from a hydroxyl radical and C1–C4 alkoxy radicals, wherein at least one of the radicals $R_1$ and $R_2$ is chosen from alkoxy radicals.

For example, the alkoxy radical may be a methoxy radical.

The hydroxyl/alkoxy molar ratio may range, for example, from 1:0.8 to 1:1.1, for example, from 1:0.9 to 1:1, and further, for example, may be 1:0.95.

The at least one aminosilicone of formula (II) may have a weight-average molecular mass, for example, ranging from 2000 to 200 000, and further, for example, from 5000 to 100 000, and still further, for example, from 10 000 to 50 000.

The weight-average molecular masses of these aminosilicones are measured by Gel Permeation Chromatography (GPC) at room temperature, as polystyrene equivalents. The columns used are styragel $\mu$ columns. The eluent is THF and the flow rate is 1 ml/minute. 200 $\mu$l of a solution at 0.5% by weight of silicone in THF are injected. The detection is performed by refractometry and UV-metry.

A commercial product comprising at least one aminosilicone chosen from formulae (I) and (II) may further comprise at least one aminosilicone other than those of formulae (I) and (II).

A product comprising at least one aminosilicone of structure (I) is sold, for example, by the company Wacker under the name Belsil ADM 652®.

A product comprising at least one aminosilicone of structure (II) is sold, for example, by the company Wacker under the name Fluid WR 1300®.

In another new embodiment, the at least one aminosilicone may be in the form of an an oil-in-water emulsion. The oil-in-water emulsion may comprise at least one surfactant. The at least one surfactant may be chosen from cationic and non-ionic surfactants.

The at least one aminosilicone particles in the emulsion may have a mean size ranging from, for example, 3 to 500 nanometers. Such particle sizes are measured with a laser granulometer.

For example, for the at least one aminosilicone of formula (II), particles in microemulsions may range in size from 5 to 60 nanometers, and, for example, from 10 to 50 nanometers.

A microemulsion comprising at least one aminosilicone of formula (II) is sold, for example, under the name Finish CT 96 E® or SLM 28020® by the company Wacker.

The at least one aminosilicone chosen from formulae (I) and (II) may be chosen such that the contact angle with water of a hair treated with a composition comprising 2% AM (active materials) of the at least one aminosilicone ranges from 90 to 180°, for example, from 90 to 130°.

A composition comprising the at least one aminosilicone chosen from formulae (I) and (II) may be chosen such that the contact angle of a hair treated with the composition ranges from 90 to 180°, for example, from 90 to 130°.

The contact angle measurement is based on immersing a hair in distilled water. The measurement may be derived from evaluating the force exerted by the water on the hair during its immersion in distilled water and during its removal. The forces are directly linked to the contact angle $\theta$ between the water and the surface of the hair. The hair is hydrophilic when the angle $\theta$ ranges from 0 to less than 90°, and hydrophobic when this angle ranges from 90 to 180°.

The test is carried out with locks of natural hair that have been bleached under the same conditions and then washed. Each 1 gram lock is placed in a crystallizing dish 75 mm in diameter and then covered uniformly with 5 ml of the test formulation. The lock is thus left for 15 minutes at room temperature and then rinsed for 30 seconds. The drained lock is left in the open air until it is completely dry.

For each evaluation, 10 hairs that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of the hair is measured by means of observation by microscope.

The mean wettability force on 10 hairs and the cross section of the analysed hairs make it possible to obtain the contact angle of the hair on the water, for example, according to the formula:

$$F = P*[lv* \cos\theta$$

where F is the wettability force expressed in newtons, P is the perimeter of the hair in meters, [lv is the liquid/water vapour interface tension in J/m², and $\theta$ is the contact angle.

For example, the product SLM 28020® from Wacker at 12% in water (i.e., 2% active materials) gives a contact angle of 93° according to the test indicated above.

The at least one aminosilicone chosen from formulae (I) and (II) may be, for example, used in a pretreatment composition in an amount ranging from 0.01% to 20% by weight relative to the total weight of the composition. For example, this amount may range from 0.1% to 15% by weight, and further, for example, from 0.5% to 10% by weight.

A pretreatment composition may comprise, for example, any ingredient used in cosmetics, such as in the art of haircare. In particular, a composition may comprise at least one surfactant and/or at least one polymer. The at least one surfactant and/or at least one polymer may be chosen from nonionic, cationic, anionic and amphoteric compounds. The at least one polymer may be chosen, for example, from aminosilicones other than those of formulae (I) and (II).

A pretreatment composition may have a pH ranging from 2 to 11, for example, from 4 to 9.

A pre-treatment composition may be chosen, for example, from forms comprising lotions, gels, creams, shampoos, sticks, mousses and sprays. At least one of these forms may be contained in a package chosen, for example, from pump-dispenser bottles and aerosol containers. If in the form of an aerosol, for example, the composition may further comprise at least one propellant chosen, for example, from alkanes, dimethyl ether, nitrogen, nitrous oxide, carbon dioxide, and haloalkanes.

Another new embodiment comprises the composition in the form of an shampoo.

The composition may comprise, for example, at least one surfactant, such as at least one anionic surfactant. The composition may comprise at least one anionic surfactant in combination with at least one additional surfactant chosen from, for example, nonionic and amphoteric surfactants.

A pretreatment composition may be used, for example, in rinse-out or leave-in mode, e.g., its application may or may not be followed by a rinsing operation.

If the composition is used in rinse-out mode, the acting time of the pretreatment composition may range from a few seconds to 60 minutes, for example, from 30 seconds to 15 minutes.

The application temperature of the pretreatment composition may range, for example, from 10 to 70° C. The application may be carried out, for example, at a temperature ranging from 10 to 60° C., for example at room temperature.

In another new embodiment, a dye composition may comprise, for example, at least one dye chosen from direct dyes and oxidation dyes.

In the case of colorations with at least one direct dye (for example, in the presence or absence of at least one oxidizing agent), the dye composition may comprise, for example, at least one dye chosen from neutral, acidic and cationic nitrobenzene direct dyes, neutral, acidic and cationic azo and methine direct dyes, neutral, acidic and cationic quinines, such as anthraquinone direct dyes, azine direct dyes, triarylmethane direct dyes, indoamine direct dyes and natural direct dyes, and mixtures thereof.

In an embodiment comprising at least one oxidation dye, the dye composition may comprise at least one oxidation base.

The at least one oxidation base may be chosen, for example, from oxidation bases used in oxidation dyeing, such as ortho- and para-phenylenediamines, double bases, ortho- and para-aminophenols, heterocyclic bases, and acid addition salts thereof.

An oxidation dye composition may comprise, for example, at least one coupler.

The at least one coupler may be chosen, for example, from couplers used in oxidation dye compositions, such as meta-phenylenediamines, meta-aminophenols and meta-diphenols, mono- and polyhydroxylated naphthalene derivatives, sesamol and its derivatives, and heterocyclic compounds, for example, indole couplers, indoline couplers and pyridine couplers, and the acid addition salts thereof.

In another embodiment, a composition may comprise, for example, at least one oxidizing agent.

The at least one oxidizing agent may be chosen, for example, from hydrogen peroxide, urea peroxide, alkali metal bromates and ferricyanides, and persalts such as perborates and persulphates. The at least one oxidizing agent may be chosen, for example from redox enzymes, such as laccases, peroxidases and 2-electron oxidoreductases (such as uricase), where appropriate in the presence of the respective donors and cofactors thereof.

Illustrative, non-limiting examples follow.

EXAMPLES

Pretreatment compositions A, B, C below were prepared. (expressed as grams of Active Material)

| Composition A | |
|---|---|
| Polydimethylsiloxane of formula (II): SLM 28020/2 ® from the company Wacker | 2 |
| Demineralized water | qs 100 |

| Composition B | |
|---|---|
| Polydimethylsiloxane of formula (II): Finish CT 96 E ® from the company Wacker | 2 |
| Demineralized water | qs 100 |

| Composition C | |
|---|---|
| Polydimethylsiloxane of formula (II): Finish WR 1300 ® from the company Wacker | 2 |
| Cetylstearyl alcohol/sodium lauryl sulphate/cetyl myristate/myristyl alcohol (62/20/8/10) | 12 |
| Glycerol | 0.5 |
| Oxyethylenated (20 EO) oleyl alcohol | 0.1 |
| Demineralized water | qs 100 |

Composition A was applied to a lock of grey hair comprising 90% white hairs. After leaving it to act for 5 minutes, and without intermediate rinsing, the lock was dyed with a commercial oxidation dye Majirel® from the company L'Oréal.

The porosity of the hair and its alkaline solubility were then evaluated by means of the methods described above.

The following results were obtained:

Majirel® coloration:

Porosity=24±1

Alkaline solubility: 9.4±0.5

Pretreatment followed by Majirel® coloration:

Porosity: 19±4

Alkaline solubility: 5.8±0.5

Control: untreated uncoloured hair:

Porosity: 17±1

Alkaline solubility: 6.3±0.7.

Hair that has undergone a pretreatment was thus less degraded.

Composition B was applied to the hair of 8 models.

Without rinsing, a commercial oxidation dye Karizma Creme Colour® from the company Soft Sheen was then applied.

It was found that, after the treatment, the hair was soft, light and easy to disentangle.

The results were superior to those that were obtained, comparatively, using the pretreatment before coloration with the range Karizma Creme Colour, a commercial pretreatment not comprising at least one aminosilicone chosen from formulae (I) and (II).

Composition B was also applied for 15 minutes at 60° C. to moderately bleached hair. The hair was then rinsed.

The following were then applied to this hair:

firstly, a direct dye Expression®, coppery shade, from the company L'Oréal (15-minute action time);

secondly, a mixture of para-phenylenediamine at $3 \times 10^{-3}$ mol/100 g and 2,4-diaminophenoxyethanol dihydrochloride at $3 \times 10^{-3}$ mol/100 g in a standard commercial oxidation dye base Recital® from the company L'Oréal, which was mixed weight-for-weight with 20-volumes aqueous hydrogen peroxide solution before the application (30-minute application time of the mixture).

The intensity of rise was then evaluated by means of the $L^*$ colorimetric parameter of the $L^*a^*b^*$ system. The following results were obtained:

| Expression ®: | Pretreatment with silicone: | $L^* = 38$ |
|---|---|---|
| | Pretreatment with water: | $L^* = 40$ |
| Recital ®: | Pretreatment with silicone: | $L^* = 16$ |
| | Pretreatment with water: | $L^* = 20$ |

These significant results showed a better rise with the pretreatment (the intensity is proportionately greater the smaller the value of $L^*$).

Composition C was applied for 10 minutes to natural hair, and was then rinsed out. A standard commercial oxidation dye was then applied. Finally, the condition of the hair was satisfactory and the cosmetic properties were good (softness and smoothness).

What is claimed is:

1. A process for pretreating keratin fibres prior to dyeing the fibres in a coloring process using at least one dye chosen from direct dyes and oxidation dyes, comprising applying to the keratin fibres a pretreatment composition comprising at least one aminosilicone chosen from formulae (I) and (II):

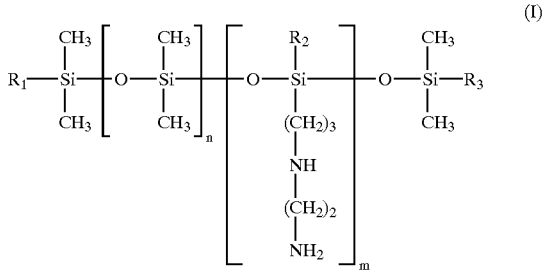

wherein:
m and n are numbers with a sum (n+m) ranging from 1 to 1000, n is a number ranging from 0 to 999, and m is a number ranging from 1 to 1000; and $R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

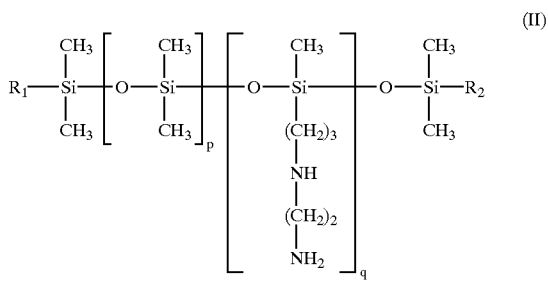

wherein:
p and q are numbers with a sum (p+q) ranging from 1 to 1000,
p is a number ranging from 0 to 999, and q is a number ranging from 1 to 1000; and $R_1$ and $R_2$, which are different, are chosen from a hydroxyl radical and $C_1$–$C_4$ alkoxy radicals, wherein at least one of the radicals $R_1$ and $R_2$ is chosen from alkoxy radicals.

2. The process according to claim 1, wherein the keratin fibres are hair.

3. The process according to claim 1, wherein the sum (m+n) ranges from 50 to 250.

4. The process according to claim 1, wherein the sum (m+n) ranges from 100 to 200.

5. The process according to claim 1, wherein n ranges from 49 to 249.

6. The process according to claim 1, wherein n ranges from 125 to 175.

7. The process according to claim 1, wherein m ranges from 1 to 10.

8. The process according to claim 1, wherein m ranges from 1 to 5.

9. The process according to claim 1, wherein the sum (p+q) ranges from 50 to 350.

10. The process according to claim 1, wherein the sum (p+q) ranges from 150 to 250.

11. The process according to claim 1, wherein p ranges from 49 to 349.

12. The process according to claim 1, wherein p ranges from 159 to 239.

13. The process according to claim 1, wherein q ranges from 1 to 10.

14. The process according to claim 1, wherein q ranges from 1 to 5.

15. The process according to claim 1, wherein the $C_1$–$C_4$ alkoxy radical is a methoxy radical.

16. The process according to claim 1, wherein the at least one aminosilicone is chosen from formula (I) and has a hydroxyl/alkoxy molar ratio ranging from 0.2:1 to 0.4:1.

17. The process according to claim 1, wherein the at least one aminosilicone is chosen from formula (I) and has a hydroxyl/alkoxy molar ratio ranging from 0.25:1 to 0.35:1.

18. The process according to claim 1, wherein the at least one aminosilicone is chosen from formula (I) has a hydroxyl/alkoxy molar ratio of 0.3:1.

19. The process according to claim 1, wherein the at least one aminosilicone is chosen from formula (II) and has a hydroxyl/alkoxy molar ratio ranging from 1:0.8 to 1:1.1.

20. The process according to claim 1, wherein the at least one aminosilicone is chosen from formula (II) and has a hydroxyl/alkoxy molar ratio ranging from 1:0.9 to 1:1.

21. The process according to claim 1, wherein the at least one aminosilicone is chosen from formula (II) and has a hydroxyl/alkoxy molar ratio of 1:0.95.

22. The process according to claim 1, wherein the at least one aminosilicone is chosen from formula (I) and has a weight-average molecular mass ranging from 2000 to 1 000 000.

23. The process according to claim 22, wherein the at least one aminosilicone is chosen from formula (I) and has a weight-average molecular mass ranging from 3500 to 200 000.

24. The process according to claim 1, wherein the at least one aminosilicone is chosen from formula (II) and has a weight-average molecular mass ranging from 2000 to 200 000.

25. The process according to claim 24, wherein the at least one aminosilicone is chosen from formula (II) and has a weight-average molecular mass ranging from 5000 to 100 000.

26. The process according to claim 25, wherein the at least one aminosilicone is chosen from formula (II) and has a weight-average molecular mass ranging from 10000 to 50 000.

27. The process according to claim 1, wherein the at least one aminosilicone is in the form of an oil-in-water emulsion and further comprises at least one surfactant.

28. The process according to claim 27, wherein the at least one surfactant is chosen from cationic and nonionic surfactants.

29. The process according to claim 27, wherein the particle size of the at least one aminosilicone in the emulsion ranges from 3 to 500 nanometers.

30. The process according to claim 29, wherein the particle size of the at least one aminosilicone in the emulsion ranges from 5 to 60 nanometers.

31. The process according to claim 30, wherein the particle size of the at least one aminosilicone in the emulsion ranges from 10 to 50 nanometers.

32. The process according to claim 1, wherein the at least one aminosilicone is chosen such that the contact angle with water of hair treated with a pretreatment composition comprising 2% AM (active materials) of said at least one aminosilicone ranges from 90 to 180°.

33. The process according to claim 32, wherein the at least one aminosilicone is chosen such that the contact angle with water of hair treated with a pretreatment composition comprising 2% AM (active materials) of said aminosilicone ranges from 90 to 130°.

34. The process according to claim 1, wherein the pretreatment composition comprising at least one aminosilicone is chosen such that a contact angle of hair treated with the pretreatment composition ranges from 90 to 180°.

35. The process according to claim 34, wherein the at least one aminosilicone is present in an amount ranging from 0.01% to 20% by weight, relative to the total weight of the pretreatment composition.

36. The process according to claim 35, wherein the at least one aminosilicone is present in an amount ranging from 0.1% to 15% by weight, relative to the total weight of the pretreatment composition.

37. The process according to claim 36, wherein the at least one aminosilicone is present in an amount ranging from 0.5% to 10% by weight, relative to the total weight of the pretreatment composition.

38. The process according to claim 1, wherein the pretreatment composition is in a form chosen from lotions, gels, creams, shampoos, sticks, mousses and sprays.

39. The process according to claim 1, wherein the pretreatment composition is packaged in a form chosen from pump-dispenser bottles and aerosol containers.

40. The process according to claim 39, wherein the pretreatment composition further comprises at least one propellant chosen from alkanes, dimethyl ether, nitrogen, nitrous oxide, carbon dioxide and haloalkanes.

41. The process according to claim 1, wherein the pretreatment composition further comprises at least one surfactant chosen from nonionic, cationic, anionic and amphoteric surfactants.

42. The process according to claim 41, wherein the pretreatment composition comprises at least one anionic surfactant and at least one additional surfactant chosen from nonionic and amphoteric surfactants.

43. The process according to claim 1, wherein the pretreatment composition comprises at least one polymer chosen from polymers other than the aminosilicones formulae (I) and (II).

44. The process according to claim 43, wherein the at least one polymer is chosen from nonionic, cationic, anionic and amphoteric polymers.

45. The process according to claim 1, wherein the pretreatment composition has a pH ranging from 2 to 11.

46. The process according to claim 45, wherein the pH ranges from 4 to 9.

47. The process according to claim 1, wherein the pretreatment composition is applied in an amount effective to improve the rise of the coloration of the fibres.

48. The process according to claim 47, wherein the fibres comprise sensitized hair.

49. The process according to claim 48, wherein the pretreatment composition is applied in an amount effective to improve at least one condition of the fibres after the fibres have been coloured with at least one oxidizing agent.

50. The process according to claim 49, wherein the process reduces the porosity of the fibres.

51. The process according to claim 49, wherein the process reduces the alkaline solubility of the fibres.

52. The process according to claim 1, wherein the process improves the resistance of the coloration of the keratin fibres with respect to shampooing.

53. A process for colouring keratin fibres, comprising: (a) applying to the fibres a pretreatment composition comprising at least one aminosilicone chosen from formulae (I) and (II):

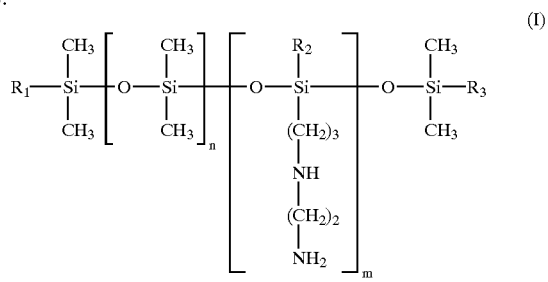

wherein:
m and n are numbers with a sum (n+m) ranging from 1 to 1000, n is a number ranging from 0 to 999, and m is a number ranging from 1 to 1000; and $R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

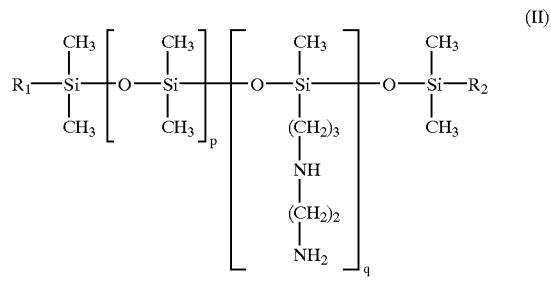

wherein:
p and q are numbers with a sum (p+q) ranging from 1 to 1000,
p is a number ranging from 0 to 999, and q is a number ranging from 1 to 1000; and
$R_1$ and $R_2$, which are different, are chosen from a hydroxyl radical and $C_1$–$C_4$ alkoxy radicals, wherein at least one of the radicals $R_1$ and $R_2$ is chosen from alkoxy radicals;

(b) optionally rinsing the fibres;
(c) applying a direct dye composition comprising at least one direct dye;
(d) leaving the direct dye composition to act for a time sufficient to develop a colour;
(e) optionally rinsing the fibres; and
(f) and optionally drying the fibres.

54. The process according to claim 53, further comprising leaving the pretreatment composition for a time to act ranging from a few seconds to 60 minutes.

55. The process according to claim 54, wherein the time to act ranges from 30 seconds to 15 minutes.

56. A process for colouring keratin fibres comprising:
(a) applying to the fibres a pretreatment composition comprising at least one aminosilicone chosen from formulae (I) and (II):

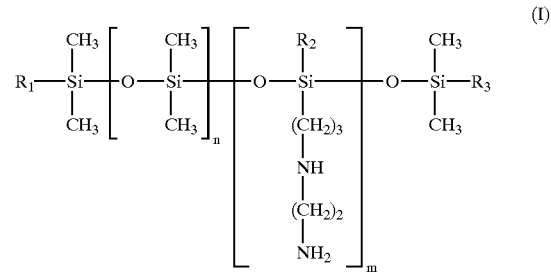

wherein:
m and n are numbers with a sum (n+m) ranging from 1 to 1000, n is a number ranging from 0 to 999, and m is a number ranging from 1 to 1000; and
$R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

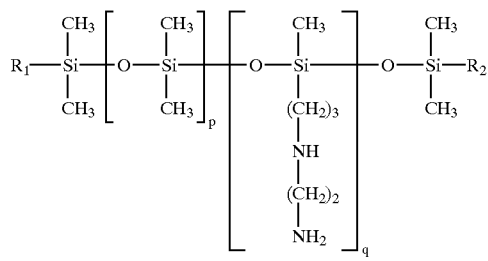
(II)

wherein:
p and q are numbers with a sum (p+q) ranging from 1 to 1000,
p is a number ranging from 0 to 999, and q is a number ranging from 1 to 1000; and $R_1$ and $R_2$, which are different, are chosen from a hydroxyl radical and $C_1$–$C_4$ alkoxy radicals, wherein at least one of the radicals $R_1$ and $R_2$ is chosen from alkoxy radicals;

(b) optionally rinsing the fibres;
(c) applying an oxidation dye composition comprising at least one oxidizing dye agent;
(d) leaving the oxidation dye composition to act for a time sufficient to develop a colour;
(e) optionally rinsing the fibres; and
(f) and optionally drying the fibres.

57. The process according to claim 56, further comprising leaving the pretreatment composition for a time to act ranging from a few seconds to 60 minutes.

58. The process according to claim 57, wherein the time to act ranges from 30 seconds to 15 minutes.

* * * * *